United States Patent [19]

Shida et al.

[11] Patent Number: 4,973,353
[45] Date of Patent: * Nov. 27, 1990

[54] 1,5-DIPHENYL-1H-1,2,4-TRIAZOLE-3-CARBOXAMIDE DERIVATIVES AND HERBICIDAL COMPOSITION CONTAINING THE SAME

[75] Inventors: Takafumi Shida; Hideo Arabori; Takeo Watanabe; Yoshikazu Kubota; Isao Ichinose; Yoichi Kanda; Shiro Yamazaki; Hiroyasu Shinkawa, all of Iwaki, Japan

[73] Assignee: Kureha Kagaku Kogyo Kabushiki Kaisha, Tokyo, Japan

[*] Notice: The portion of the term of this patent subsequent to Apr. 24, 2007 has been disclaimed.

[21] Appl. No.: 162,699

[22] Filed: Mar. 1, 1988

[30] Foreign Application Priority Data

Mar. 10, 1987 [JP] Japan ................................. 62-54579
Jun. 19, 1987 [JP] Japan ................................. 62-153031

[51] Int. Cl.$^5$ ................. A01N 43/653; C07D 249/08
[52] U.S. Cl. ....................................... 71/92; 548/266.8
[58] Field of Search .................. 548/262, 266.8; 71/92

[56] References Cited

U.S. PATENT DOCUMENTS 4,492,597  1/1985  Aoki et al. .............................. 71/92
4,795,484  1/1989  Aoki et al. .............................. 71/92
4,820,334  4/1989  Shida et al. ......................... 548/262

FOREIGN PATENT DOCUMENTS 2120665B  12/1985  United Kingdom ..................... 71/92

OTHER PUBLICATIONS

*Chemical Abstracts*, vol. 100, No. 19, Column 1, Abstract No. 156607x, Kureha Chemical Ind. Co.

*Primary Examiner*—Glennon H. Hollrah
*Assistant Examiner*—Patricia L. Morris
*Attorney, Agent, or Firm*—Nixon & Vanderhye

[57] ABSTRACT

Disclosed herein is a derivative of 1,5-diphenyl-1H-1,2,4-triazole-3-carboxamide represented by the formula (I):

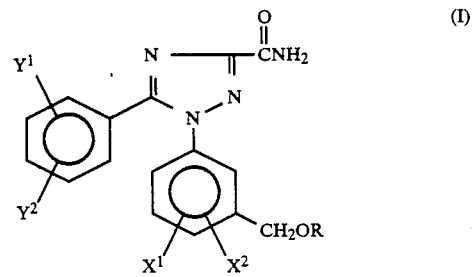

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; and $Y^2$ is a hydrogen or a fluorine, and the herbicidal compositions containing said derivatives as active ingredient therefor.

The derivative of 1,5-diphenyl-1H-1,2,4-triazole-3-carboxamide represented by the formula (I) of the present invention is the compound having high herbicidal activity and also showing excellent selectivity for killing weeds alone without doing any serious harm to the crops such as rice, wheat and corn.

10 Claims, No Drawings

1,5-DIPHENYL-1H-1,2,4-TRIAZOLE-3-CARBOXAMIDE DERIVATIVES AND HERBICIDAL COMPOSITION CONTAINING THE SAME

BACKGROUND OF THE INVENTION

The present invention relates to the derivatives of 1,5-diphenyl-1H-1,2,4-triazole-3-carboxamide usable as an active ingredient of herbicides, and to the herbicidal compositions containing such derivatives.

Rice, wheat and corn are the important farm products, and use of herbicides is essential for protecting these crops from harm by weeds so as to attain an increased yield.

It is known that the derivatives of 1,5-diphenyl-1H-1,2,4-triazole-3-carboxamide have a herbicidal activity. For instance, Japanese Patent Application Kokai (Laid-Open) No. 193406/82 discloses a herbicidal composition containing as its active ingredient a derivative of 1,2,4-triazole represented by the formula:

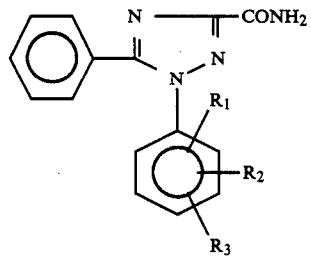

wherein $R_1$ is a hydrogen atom, a fluorine atom, a chlorine atom, an iodine atom, a lower alkyl group having 1 to 3 carbon atoms, an alkyl group substituted with fluorine, a nitro group or a methoxy group; $R_2$ is a hydrogen atom, a chlorine atom or a methyl group; and $R_3$ is a hydrogen atom or a methyl group.

Also, in Japanese Patent Application Kokai (Laid-Open) No. 98004/84 is disclosed a herbicidal composition containing a derivative of 1,2,4-triazole represented by the formula (I):

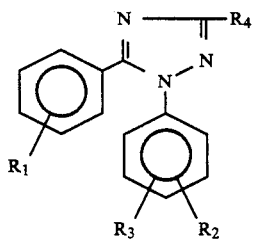

wherein $R_1$ and $R_2$ represent independently a hydrogen atom, a halogen atom, an alkyl group or a halogenoalkyl group; $R_3$ is a hydrogen atom, a halogen atom or an alkyl group; and $R_4$ is a cyano, carbamoyl, thiocarbamoyl, N-alkylcarbamoyl, N-halogenoalkylcarbamoyl, N-methoxyalkylcarbamoyl, N-alkenylcarbamoyl, N-halogenoalkenylcarbamoyl, N-acylcarbamoyl, N-halogenoacylcarbamoyl or N-methylthiocarbamoylcarbamoyl group.

These derivatives, however, are still unsatisfactory in herbicidal activity and selectivity. Therefore, development of the compounds having high herbicidal activities and excellent selectivity enabling killing of weeds alone without doing any harm to the crops such as rice, wheat, corn, etc., has been strongly desired.

The present inventors have made studies for providing a compound showing a high herbicidal activity but being practically harmless to such crops as rice, wheat and corn, and found that the derivatives of 1,5-diphenyl-1H-1,2,4-triazole-3-carboxamide represented by the following formula (I) have the excellent selective herbicidal activity:

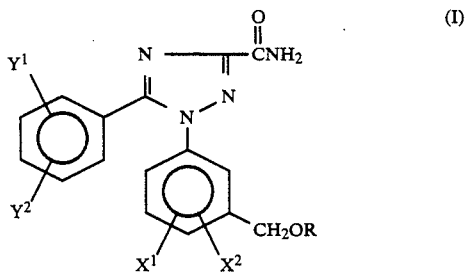

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; and $Y^2$ is a hydrogen or a fluorine. The present invention was achieved on the basis of this finding.

The compounds of the formula (I) are different from the compounds disclosed in aforementioned Japanese Patent Application Kokai (Laid-Open) Nos. 193406/82 and 98004/84 in that the compound of the formula (I) has an $X^1$ group and a 3-position —CH$_2$OR group ($X^1$ and R having the same meanings as defined above) on the 1-position phenyl group of 1,5-diphenyl-1H-1,2,4-triazole-3-carboxamide. These compounds are not found in the prior literatures.

Thus, the present invention has for its object to provide the derivatives of 1,5-diphenyl-1H-1,2,4-triazole-3-carboxamide having excellent selective herbicidal activities against grass weeds and, in particular, broadleaf weeds while doing no harm to such crops as rice, wheat and corn, and the herbicidal compositions containing the derivative as active ingredient.

SUMMARY OF THE INVENTION

In a first aspect of the present invention, there is provided a derivative of 1,5-diphenyl-1H-1,2,4-triazole-3-carboxamide represented by the formula (I):

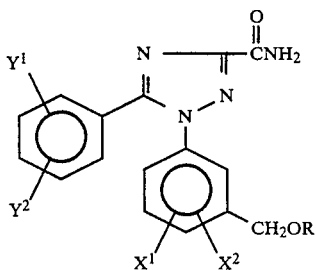

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; and $Y^2$ is a hydrogen or a fluorine.

In a second aspect of the present invention, there is provided a herbicidal composition containing as active ingredient a herbicidally effective amount of a derivative of 1,5-diphenyl-1H-1,2,4-triazole-3-carboxamide represented by the formula (I):

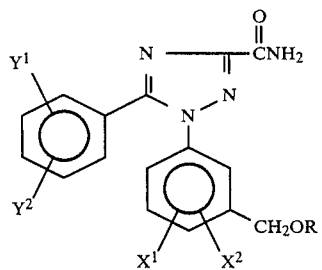

wherein R, $X^1$, $X^2$, $Y^1$ and $Y^2$ are as defined above.

In a third aspect of the present invention, there is provided a process for preparing a derivative of 1,5-diphenyl-1H-1,2,4-triazole-3-carboxamide represented by the formula (I):

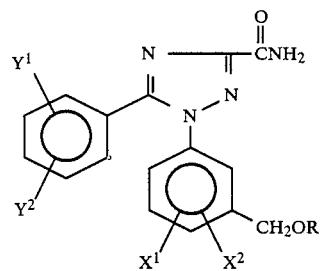

wherein R, $X^1$, $X^2$, $Y^1$ and $Y^2$ are as defined above, which comprises reacting a derivative of 2-phenyl-4-(phenylhydrazono)-2-oxazolin-5-one represented by the formula (II):

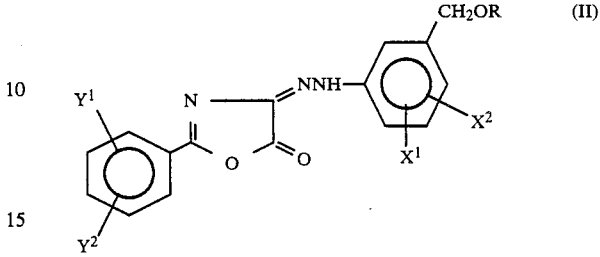

wherein R, $X^1$, $X^2$, $Y^1$ and $Y^2$ are as defined above, and ammonia in an organic solvent at a temperature of $-10°$ to $150°$ C., acidifying the resulting reaction mixture to subject the resulting product to dehydrating-cyclization.

DETAILED DESCRIPTION OF THE INVENTION

The present invention relates to a derivative of 1,5-diphenyl-1H-1,2,4-triazole-3-carboxamide represented by the formula (I):

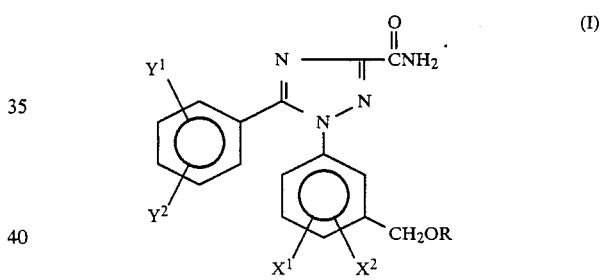

and a herbicidal composition containing the derivative as active ingredient.

In the above formula (I), R represents a straight-chain alkyl group having 1 to 10, preferably 2 to 6 carbon atoms which is non-substituted or substituted with 1 to 19, preferably 3 to 12 fluorine atoms, a branched alkyl group having 3 to 10, preferably 4 to 7 carbon atoms which is non-substituted or substituted with 1 to 19, preferably 3 to 12 fluorine atoms, a cyclic alkyl group having 3 to 10, preferably 5 to 7 carbon atoms, an alkyl group having 1 to 3 carbon atoms which is substituted with an alicyclic structure having 3 to 7 carbon atoms, a phenyl group, or an aralkyl group having 7 to 9 carbon atoms. $X^1$ represents a halogen or an alkyl group having 1 to 3 carbon atoms. $X^2$ represents a hydrogen, a halogen or an alkyl group having 1 to 3 carbon atoms. $Y^1$ represents a hydrogen or a fluorine. $Y^2$ represents a hydrogen or a fluorine.

Illustrative examples of the compounds of formula (I) according to the present invention and their physicochemical properties are shown in Table 1. The results of elemental analyses of these compounds are shown in Table 2.

TABLE 1

| No. | R | X¹ | X² | Y¹ | Y² | Yield of synthesis (%) | Melting point (°C.) | NMR spectrum (CDCl₃, δ, ppm, 60MHz) |
|---|---|---|---|---|---|---|---|---|
| 1 | —CH₂CH₃ | 4-Cl | H | H | H | 77.5 | 127~129 | 1.13(3H,t,7Hz),3.47(2H,q,7Hz), 4.56(2H,s), 6.6~7.6(10H,m) |
| 2 | —(CH₂)₃CH₃ | 4-Cl | H | H | H | 94.2 | 96~98 | 1.00(3H,t,6Hz), 1.13~1.85(4H,m), 3.46(2H,t,6Hz), 4.52(2H,s), 6.9~7.9(10H,m) |
| 3 | —(CH₂)₄CH₃ | 4-Cl | H | H | H | 84.6 | 133~135 | 0.85(3H,t,6Hz), 1.05~1.73(6H,m), 3.30(2H,t,6Hz), 4.43(2H,s), 6.3(1H,bs), 6.8~7.5(9H,m) |
| 4 | —(CH₂)₂CH(CH₃)₂ | 4-Cl | H | H | H | 95.7 | 121~123 | 0.87(6H,d,6Hz), 1.20~2.00(3H,m), 3.50(2H,t,6Hz) 4.53(2H,s), 6.68(1H,bs), 7.20(1H,bs), 7.3~7.8(8H,m) |
| 5 | —CH₂—C(CH₃)₃ | 4-Cl | H | H | H | 89.0 | 115~118 | 0.81(9H,s), 3.05(2H,s), 4.50(2H,s), 6.3(1H,bs) 6.9~7.6(9H,m) |
| 6 | —(CH₂)₅CH₃ | 4-Cl | H | H | H | 87.2 | 118~119 | 0.87(3H,t,6Hz), 1.0~2.1(8H,m), 3.41(2H,t,6Hz), 4.53(2H,s), 2.6(1H,bs), 7.0~7.8(9H,m) |
| 7 | —(CH₂)₇CH₃ | 4-Cl | H | H | H | 74.5 | 104~107 | 0.86(3H,m), 1.06~1.66(12H,m), 3.41(2H,t,6Hz), 4.50(2H,s), 6.35(1H,bs), 7.0–7.6(9H,m) |
| 8 | —CH₂-cyclohexyl | 4-Cl | H | H | H | 82.5 | 138~140 | 0.6~1.9(11H,m), 3.19(2H,d,6Hz), 4.47(2H,s), 6.6~7.9(10H,m) |
| 9 | —phenyl | 4-Cl | H | H | H | 77.3 | 164~166 | 5.10(2H,s), 6.2(1H,bs), 6.7~7.7(14H,m) |
| 10 | —CH₂-phenyl | 4-Cl | H | H | H | 85.0 | 96~98 | 4.50(2H,s), 4.56(2H,s), 6.6~7.7(15H,m) |
| 11 | —CH₂CF₃ | 4-Cl | H | H | H | 78.0 | 114~116 | 3.88(2H,q,9Hz), 4.80(2H,s), 7.0~7.8(10H,m) |
| 12 | —CH₂CF₂CHF₂ | 4-Cl | H | H | H | 93.3 | 117~119 | 3.78(2H,tt,13,2Hz), 4.66(2H,s), 5.76(1H,tt,54,5Hz) 7.3~7.8(10H,m) |
| 13 | —CH₂CF₂CF₃ | 4-Cl | H | H | H | 80.8 | 138~140 | 3.78(2H,tq,13,2Hz), 4.73(2H,s), 6.6~7.8(10H,m) |
| 14 | —CH₂CF₂CHFCF₃ | 4-Cl | H | H | H | 92.5 | 94~96 | 3.20~4.13(2H,m), 4.75(2H,s), 5.32(1H,d,6-plet, 50,6Hz), 6.82(1H,bs), 7.30(1H,bs), 7.4~7.8(8H,m) |
| 15 | —CH₂(CF₂)₂CF₃ | 4-Cl | H | H | H | 87.2 | 135~136 | 3.97(2H,tt,13.5,2Hz), 4.74(2H,s), 6.6~7.8(10H,m) |
| 16 | —CH₂CF₂CF₃ | 4-Br | H | H | H | 72.7 | 141~143 | 3.88(2H,tq,13,1Hz), 4.67(2H,s), 6.7~7.9(10H,m) |
| 17 | —(CH₂)₂CH(CH₃)₂ | 4-Br | H | H | H | 89.4 | 128~130 | 0.85(6H,d,6Hz), 1.1~2.1(3H,m), 3.47(2H,t,6Hz), 4.46(2H,s), 6.8~7.9(10H,m) |
| 18 | —CH₂CF₂CF₃ | 4-I | H | H | H | 83.5 | 83~85 | 3.86(2H,tq,13,2Hz), 4.56(2H,s), 6.3(1H,bs), 7.06(1H,dd,8,3Hz), 7.2~7.6(7H,m), 7.85(1H,d,8Hz) |
| 19 | —CH₂CF₂CF₃ | 4-Cl | 6-Cl | H | H | 82.1 | 187~189 | 3.94(2H,tq,13,2Hz), 4.70(2H,s), 6.3~7.7(9H,m) |
| 20 | —(CH₂)₂CH(CH₃)₂ | 4-Cl | 6-Cl | H | H | 91.4 | 126~128 | 0.87(6H,d,6Hz), 1.2~1.9(3H,m), 3.52(2H,t,6Hz), 4.53(2H,s), 6.2(1H,bs), 6.9~7.9(8H,m) |
| 21 | —CH₂CF₂CF₃ | 2-Cl | H | H | H | 89.7 | 113~115 | 3.96(2H,tq,13,2Hz), 4.70(2H,s), 7.2~7.7(10H,m)* |
| 22 | —CH₂CF₂CF₃ | 6-Cl | H | H | H | 74.5 | 213~215 | 3.97(2H,tq,13,2Hz), 4.73(2H,s), 6.1~7.8(10H,m) |
| 23 | —(CH₂)₂CH(CH₃)₂ | 4-Cl | H | 2-F | H | 82.3 | 113~115 | 0.87(6H,d,6Hz), 1.1~2.1(3H,m), 3.40(2H,t,6Hz), 4.47(2H,s), 6.5~7.9(9H,m) |
| 24 | —CH₂CF₂CF₃ | 4-Cl | H | 2-F | H | 62.8 | 104~106 | 3.87(2H,tq,13,1Hz), 4.67(2H,s), 6.7~7.8(9H,m) |

TABLE 1-continued

| No. | R | X¹ | X² | Y¹ | Y² | Yield of synthesis (%) | Melting point (°C.) | NMR spectrum (CDCl₃, δ, ppm, 60MHz) |
|---|---|---|---|---|---|---|---|---|
| 25 | —(CH₂)₂CH(CH₃)CH₃ | 4-Cl | H | 2-F | 4-F | 96.7 | 84~86 | 0.87(6H,d,6Hz), 1.2~2.0(3H,m), 3.43(2H,t,6Hz), 4.47(2H,s), 6.4(1H,bs), 6.6~7.8(7H,m) |
| 26 | —(CH₂)₂CH(CH₃)CH₃ | 4-Cl | H | 2-F | 6-F | 87.5 | 88~90 | 0.90(6H,d,6Hz), 1.2~2.0(3H,m), 3.43(2H,t,6Hz), 4.47(2H,s), 6.3(1H,bs), 6.8~7.6(7H,m) |
| 27 | —(CH₂)₂CH(CH₃)CH₃ | 4-CH₃ | H | H | H | 90.0 | 83~85 | 0.87(6H,d,6,6Hz), 1.45(2H,q,6.6Hz), 1.66(1H,m), 2.36(3H,s), 3.44(2H,t,6,6Hz), 4.44(2H,s), 5.74(1H,bs), 7.09(1H,bs), 7.15~7.60(8H,m)** |
| 28 | —CH₂CF₂CF₃ | 4-CH₃ | H | H | H | 95.5 | 127~129 | 2.37(3H,s), 3.80(2H,tq,13.2,1.0Hz), 4.62(2H,s), 5.76(1H,bs), 7.10(1H,bs), 7.2~7.6(8H,m)** |
| 29 | —CH₂CH(CH₃)CH₂CH₃ | 4-Cl | H | H | H | 66.3 | 142~143 | 0.85(3H,t,6Hz), 0.84(3H,d,6Hz), 1.0~2.25(3H,m), 3.31(2H,d,6Hz), 4.58(2H,s), 6.5(1H,bs), 7.0~7.73(9H,m) |
| 30 | —(CH₂)₃CH₃ | 4-Br | H | H | H | 65.3 | 105~106 | 0.97(3H,t,6Hz), 1.0~1.7(4H,m), 3.39(2H,t,6Hz), 4.42(2H,s), 6.4~7.6(10H,m) |
| 31 | —(CH₂)₃CH₃ | 4-Br | H | 2-F | H | 70.2 | 126~128 | 0.88(3H,t,6Hz), 1.0~1.8(4H,m), 3.37(2H,t,6Hz) 4.37(2H,s), 6.3~7.8(9H,m) |
| 32 | —CH₂CF₂CF₃ | 4-Cl | 6-F | H | H | 58.8 | 177~179 | 3.96(2H,tq,13,2Hz), 4.73(2H,s), 6.21(1H,bs) 6.9~7.6(6H,m), 7.25(1H,d,10Hz), 7.68(1H,d,8Hz) |
| 33 | —CH₂CF₃ | 4-Br | H | H | H | 52.8 | 120~122 | 3.77(2H,q,9Hz), 4.67(2H,s), 6.1~7.7(10H,m) |
| 34 | —(CH₂)₃CH₃ | 4-Cl | H | 2-F | H | 90.4 | 95~97 | 0.85(3H,t,6Hz), 1.0~1.8(4H,m), 3.32(2H,t,6Hz), 4.40(2H,s), 6.5~7.7(9H,m) |
| 35 | —CH₂CF₂CF₃ | 4-F | H | H | H | 83.6 | 141~142 | 3.85(2H,tq,14,2Hz), 4.65(2H,s), 6.4~7.7(10H,m) |
| 36 | —(CH₂)₃CH₃ | 4-CH₃ | H | H | H | 59.8 | 101~103 | 0.89(3H,t,7.3Hz), 1.32(2H,6-plet,7.3Hz), 1.53(2H,5-plet,7.3Hz), 2.36(3H,s), 3.41(2H,t,7.3Hz), 4.45(2H,s), 7.15~7.6(8H,m), 5.8(1H,bs), 7.09(1H,bs)** |
| 37 | —(CH₂)₂CH(CH₃)CH₃ | 4-CH₃ | H | 2-F | 6-F | 85.3 | Amorphous | 0.87(6H,d,6.4Hz), 1.44(2H,q,6.4Hz), 1.66(1H,9-plet, 6.4Hz), 2.30(3H,s), 3.40(2H,t,6.4Hz), 4.39(2H,s), 6.96(2H,t,8.3Hz), 7.13(1H,d,7.8Hz), 7.18(1H,dd,7.8,1.5Hz), 7.37(1H,d,1.5Hz), 7.38~7.52(1H,m), 5.87(1H,bs), 7.10(1H)** |
| 38 | —(CH₂)₂CH(CH₃)CH₃ | 4-CH₃ | H | 2-F | H | 58.5 | 94~96 | 0.87(6H,d,6.8Hz), 1.42(2H,q,6.8Hz), 1.64(1H,9-plet, 6.8Hz), 2.31(3H,s), 3.39(2H,t,6.8Hz), 4.40(2H,s), 7.03(1H,t,9.3Hz), 7.12~7.40(4H,m), 7.48(1H,m), 7.59(1H, td,7.3,2.0Hz), 5.83(1H,bs), 7.10(1H) ** |
| 39 | —CH₂CF₂CHF₂ | 4-CH₃ | H | H | H | 77.0 | 118~120 | 2.33(3H,s), 3.70(2H,tt,13,2Hz), 4.53(2H,s), 5.76(1H,tt, 53,5Hz), 6.5(1H,bs), 7.0~7.7(9H,m) |
| 40 | —CH₂CF₂CF₃ | 4-CH₃ | H | 2-F | H | 60.3 | 110~111 | 2.33(3H,s), 3.76(2H,t,13.2Hz), 4.58(2H,s), 7.04(1H,t, 9.3Hz), 7.15~7.35(4H,m), 7.4~7.55(1H,m), 7.61(1H, td,7.3,2.0Hz), 5.79(1H,bs), 7.10(1H,bs)** |
| 41 | —CH₂CF₂CF₃ | 4-CH₃ | H | 2-F | 6-F | 97.3 | 111~114 | 2.32(3H,s), 3.79(2H,t,13.2Hz), 4.58(2H,s), 6.97(2H,t, 8.3Hz), 7.20(1H,d,7.8Hz), 7.27(1H,dd,7.8,2.0Hz), 7.32 (1H,d,2.0Hz), 7.47(1H,m), 5.80(1H,bs), 7.10(1H,bs)** |
| 42 | —CH₂CF₂CHFCF₃ | 4-CH₃ | H | H | H | 68.5 | 114~115 | 2.30(3H,s), 3.36~3.96(2H,m), 4.48(2H,s), 4.96(H,d, 6-plet,43,6Hz), 6.1(1H,bs), 6.8~7.5(9H,m) |
| 43 | —CH₂(CF₂)₂CF₃ | 4-CH₃ | H | H | H | 82.1 | 116~118 | 2.35(3H,s), 3.68(2H,tq,14,2Hz), 4.60(2H,s), 6.9~7.7(10H,m) |
| 44 | —(CH₂)₂CH₃ | 4-CH₃ | H | H | H | 84.5 | 84~86 | 0.85(3H,t,6Hz), 1.53(2H,6-plet,6Hz), 2.30(3H,s), 3.28(2H,t,6Hz), 4.35(2H,s), 6.6~7.6(10H,m) |
| 45 | —(CH₂)₅CH₃ | 4-CH₃ | H | H | H | 62.3 | 78~80 | 0.87(3H,t,6Hz), 1.0~1.9(8H,m), 2.33(3H,s), 3.35(2H,t,6Hz), 4.45(2H,s), 6.4~7.6(10H,m) |
| 46 | —CH₂CF₃ | 4-CH₃ | H | H | H | 75.6 | 145~146 | 2.33(3H,s), 3.69(2H,q,8Hz), 4.57(2H,s), 6.7(1H,bs) 7.0~7.6(9H,m) |
| 47 | —CH₂(CF₂)₂CF₃ | 4-Br | H | H | H | 83.6 | 155~156 | 3.92(2H,tt,14,2Hz), 4.66(2H,s), 6.9(1H,bs), 7.0~7.6 (9H,m) |
| 48 | —CH₂CF₂CF₃ | 4-CH₂CH₃ | H | H | H | 86.6 | 114~115 | 1.21(3H,t,8Hz), 2.69(2H,q,8Hz), 3.76(2H,tq,13,2Hz) |

TABLE 1-continued

| | Substituent in formula (I)*** | | | | | Yield of synthesis (%) | Melting point (°C.) | NMR spectrum (CDCl$_3$, δ, ppm, 60MHz) |
|---|---|---|---|---|---|---|---|---|
| No. | R | X$^1$ | X$^2$ | Y$^1$ | Y$^2$ | | | |
| | | | | | | | | 4.60(2H,s), 6.7(1H,bs), 6.9∼7.8(9H,m) |

*DHSO-d$_6$ was used as solvent.
**Measured at 250 MHz.
***The substituents were numbered as shown in the following formula.

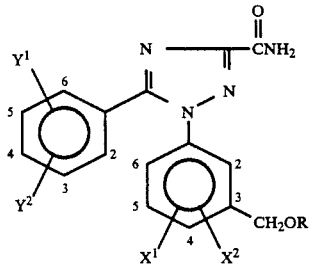

TABLE 2

| No. | Calculated | | | Found | | |
|---|---|---|---|---|---|---|
| | C (%) | H (%) | N (%) | C (%) | H (%) | N (%) |
| 1 | 60.59% | 4.80% | 15.70% | 60.76% | 4.97% | 15.87% |
| 2 | 62.42% | 5.50% | 14.56% | 62.52% | 5.60% | 14.66% |
| 3 | 63.23% | 5.81% | 14.05% | 63.30% | 5.87% | 14.11% |
| 4 | 63.23% | 5.81% | 14.05% | 63.35% | 5.93% | 14.16% |
| 5 | 63.23% | 5.81% | 14.05% | 63.40% | 5.97% | 14.21% |
| 6 | 63.99% | 6.10% | 13.57% | 64.01% | 6.12% | 13.59% |
| 7 | 65.37% | 6.63% | 12.70% | 65.30% | 6.56% | 12.63% |
| 8 | 65.01% | 5.93% | 13.18% | 64.83% | 5.75% | 13.01% |
| 9 | 65.27% | 4.23% | 13.84% | 65.15% | 4.12% | 13.72% |
| 10 | 65.95% | 4.57% | 13.37% | 65.80% | 4.42% | 13.22% |
| 11 | 52.63% | 3.44% | 13.64% | 52.48% | 3.28% | 13.49% |
| 12 | 51.54% | 3.41% | 12.65% | 51.61% | 3.49% | 12.73% |
| 13 | 49.53% | 3.06% | 12.16% | 49.33% | 2.87% | 11.97% |
| 14 | 48.75% | 3.07% | 11.37% | 48.74% | 3.06% | 11.36% |
| 15 | 47.03% | 2.76% | 10.97% | 47.23% | 2.96% | 11.17% |
| 16 | 45.17% | 2.79% | 11.09% | 45.05% | 2.68% | 10.97% |
| 17 | 56.89% | 5.23% | 12.64% | 57.06% | 5.40% | 12.80% |
| 18 | 41.33% | 2.56% | 10.15% | 41.16% | 2.39% | 9.98% |
| 19 | 46.08% | 2.65% | 11.31% | 46.27% | 2.83% | 11.50% |
| 20 | 58.21% | 5.12% | 12.93% | 58.15% | 5.06% | 12.87% |
| 21 | 49.53% | 3.06% | 12.16% | 49.33% | 2.87% | 11.97% |
| 22 | 49.53% | 3.06% | 12.16% | 49.63% | 3.17% | 12.26% |
| 23 | 60.50% | 5.32% | 13.44% | 60.31% | 5.12% | 13.24% |
| 24 | 47.67% | 2.74% | 11.70% | 47.70% | 2.77% | 11.74% |
| 25 | 58.00% | 4.87% | 12.88% | 58.03% | 4.89% | 12.91% |
| 26 | 58.00% | 4.87% | 12.88% | 58.05% | 4.91% | 12.93% |
| 27 | 69.82% | 6.92% | 14.80% | 69.95% | 7.05% | 14.93% |
| 28 | 54.55% | 3.89% | 12.72% | 54.39% | 3.37% | 12.56% |
| 29 | 63.23% | 5.81% | 14.05% | 63.50% | 6.02% | 14.16% |
| 30 | 55.95% | 4.93% | 13.05% | 56.08% | 4.74% | 13.00% |
| 31 | 53.70% | 4.51% | 12.53% | 53.63% | 4.67% | 12.38% |
| 32 | 47.66% | 2.74% | 11.70% | 47.47% | 2.54% | 11.90% |
| 33 | 47.49% | 3.10% | 12.31% | 47.67% | 2.95% | 12.49% |
| 34 | 59.63% | 5.00% | 13.91% | 59.44% | 4.92% | 14.11% |
| 35 | 51.36% | 3.18% | 12.61% | 51.38% | 3.30% | 12.76% |
| 36 | 69.21% | 6.64% | 15.37% | 69.40% | 6.78% | 15.29% |
| 37 | 63.76% | 5.84% | 13.52% | 63.69% | 5.74% | 13.56% |
| 38 | 66.65% | 6.36% | 14.13% | 66.81% | 6.55% | 14.11% |
| 39 | 56.87% | 4.30% | 13.26% | 56.91% | 4.12% | 13.46% |
| 40 | 52.41% | 3.52% | 12.22% | 52.23% | 3.71% | 12.11% |
| 41 | 50.43% | 3.17% | 11.76% | 50.40% | 3.29% | 11.84% |
| 42 | 53.39% | 3.84% | 11.86% | 53.35% | 4.04% | 11.66% |
| 43 | 51.44% | 3.49% | 11.43% | 51.24% | 3.63% | 11.57% |
| 44 | 68.55% | 6.33% | 15.99% | 68.74% | 6.48% | 15.86% |
| 45 | 70.38% | 7.19% | 14.27% | 70.43% | 7.06% | 14.35% |
| 46 | 58.56% | 4.39% | 14.35% | 58.56% | 4.35% | 14.17% |
| 47 | 43.26% | 2.54% | 10.09% | 43.07% | 2.65% | 10.23% |
| 48 | 55.51% | 4.21% | 12.33% | 55.32% | 4.32% | 12.53% |

All of these compounds have the selective herbicidal activities described above and are therefore widely applicable as active ingredient for a herbicidal composition used in a paddy field and a crop field.

The compounds of formula (I) according to the present invention can be prepared from a process according to the following Reaction Scheme 1.

Reaction Scheme 1

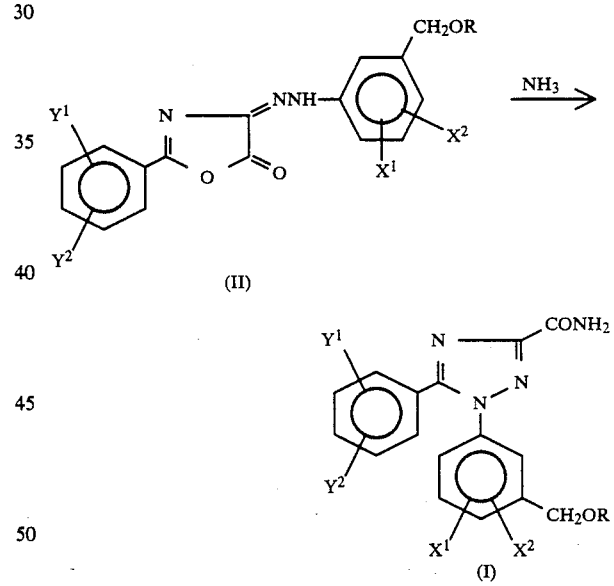

wherein R, X$^1$, X$^2$, Y$^1$ and Y$^2$ are as defined above.

A derivative of 2-phenyl-4-(phenylhydrazono)-2-oxazolin-5-one represented by the formula (II) is reacted with ammonia in an organic solvent such as acetone or toluene at a temperature of −10° to 150° C. for 0.1 to 20 hours. The resulting reaction mixture is acidified to pH 1-3 with hydrochloric acid, acetic acid or the like and then stirred at 0° to 150° C. for 0.1 to 20 hours to effect dehydration-cyclization. The process gives the compounds of formula (I) of the present invention in a high yield.

The compound of formula (II) can be synthesized, for example, by a process according to the following Reaction Scheme 2.

Reaction Scheme 2

Reaction Scheme 2

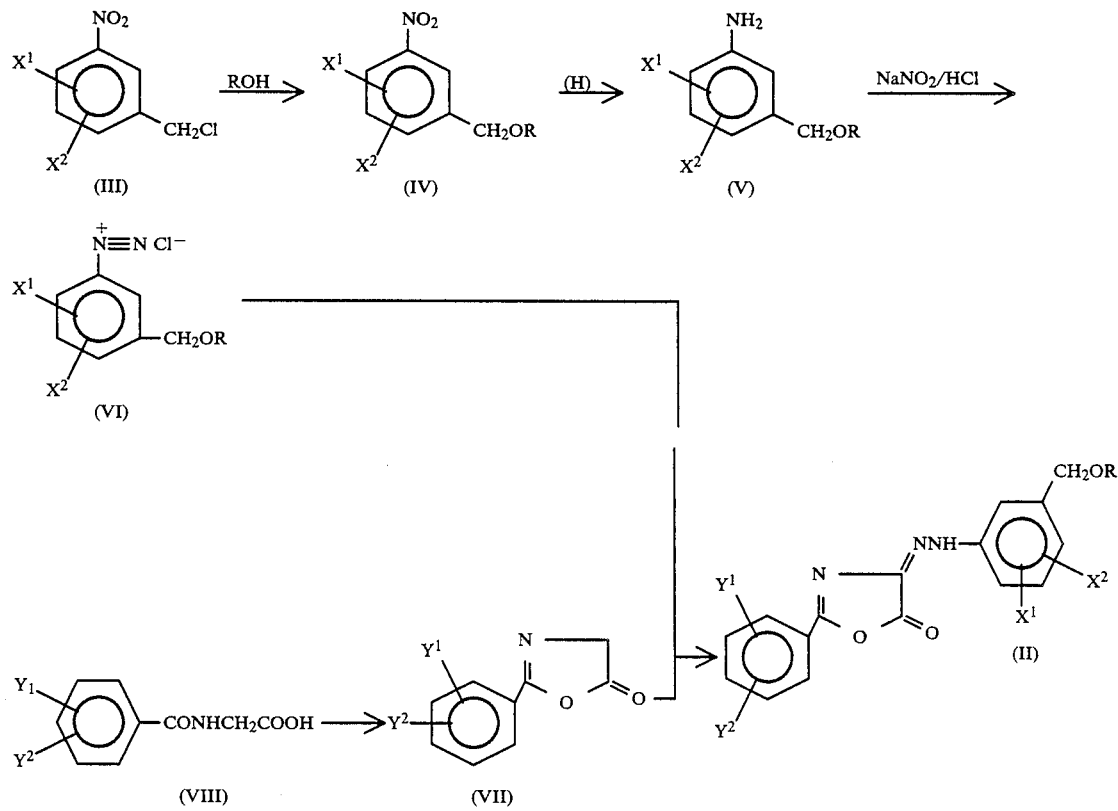

wherein R, $X^1$, $X^2$, $Y^1$ and $Y^2$ are as defined above.

A derivative of chloromethylnitrobenzene (III) is etherified by, for example, reacting it with ROH in dimethylformamide or hexamethylphosphoramide in the presence of a hydrogen chloride acceptor such as KOH or NaH at a temperature of −10° to 150° C., preferably 0° to 80° C., for 0.1 to 20 hours, preferably 0.5 to 10 hours, to synthesize a derivative of nitrobenzyl ether (IV). This derivative of nitrobenzyl ether (IV) is then reduced by a conventional method, for example, by adding thereto hydrazine hydrate in an alcohol solution thereof and heating the mixture under reflux in the presence of palladium-charcoal for 1 to 10 hours to obtain a derivative of aniline (V). Other reducing methods are also usable here, such as a method in which the derivative of nitrobenzyl ether (IV) is reduced by using iron, zinc or tin in a solvent such as hydrochloric acid or acetic acid; a method where the derivative (IV) is reduced by using colloidal sulfur or sodium sulfide in ethanol or hydrous ethanol; a method where the derivative (IV) is reduced by the action of hydrazine in ethanol in the presence of ferric salt and active carbon; and a method in which the derivative (IV) is catalytically reduced by hydrogen gas of ordinary pressure to 5 atm in a solvent such as ethanol or acetic acid in the presence of a catalyst such as Raney nickel, palladium carbon or platinum oxide.

Then the derivative of aniline (V) is converted into a diazonium salt (VI) by, for instance, using sodium nitrite in hydrochloric acid at a temperature of −10° to 15° C.

Separately, a derivative of 2-phenyl-2-oxazolin-5-one (VII) is synthesized by subjecting a derivative of hippuric acid (VIII) to dehydrating-cyclization in acetic anhydride at a temperature of 20° to 100° C., preferably 50° to 90° C., for 0.1 to 30 hours, preferably 0.1 to 3 hours. Then the diazonium salt (VI) is reacted with the derivative of 2-phenyl-2-oxazolin-5-one (VII) at a temperature of −50° to 100° C., preferably −30° to 40° C., for 0.01 to 20 hours, preferably 0.1 to 10 hours to obtain the compound represented by the formula (II).

The 1,5-diphenyl-1H-1,2,4-triazole-3-carboxamide derivatives of the present invention can be used alone or in the various forms of composition such as wettable powder, emulsion, granules, powder, etc., with various types of carrier (diluent) and/or adjuvant commonly used in the preparation of agricultural chemicals.

The concentration of 1,5-diphenyl-1H-1,2,4-triazole-3-carboxamide derivative of the present invention in the compositions is preferably in the range of 0.1 to 50% by weight.

The 1,5-diphenyl-1H-1,2,4-triazole-3-carboxamide derivatives of the present invention and the herbicidal composition containing such compounds as active ingredient are sprayed or spread on the soil of the field and/or the stalks and leaves of the plants by a known method so that the compound will be applied at a rate of preferably 0.1 to 500 g per 10 areas.

The present invention will hereinafter be described more precisely while referring the following examples, but it is to be understood that the invention is not limited by the following examples.

SYNTHESIS EXAMPLE 1

Synthesis of 3-(2,2,3,3,3-pentafluoropropoxy)methyl-4-methyl-1-nitrobenzene (the compound of formula (IV) wherein R is $CH_2CF_2CF_3$, $X^1$ is 4-$CH_3$ and $X^2$ is H)

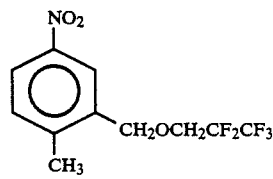

To a solution of 5.00 g (0.027 mol) of 2-methyl-5-nitrobenzyl chloride and 21.3 g (0.135 mol) of 2,2,3,3,3-pentafluoropropanol in 16.5 ml of dimethylformamide, was added 2.29 g (0.041 mol) of KOH pellets and the solution was stirred overnight. Then dichloromethane was added and the salts were filtered out. The filtrate was made acid and then the solvents were distilled off. The residue was dissolved in a 9/1 (v/v) mixed solvent of hexane/ethyl acetate, washed with dilute hydrochloric acid, water and a saturated sodium chloride aqueous solution, and then dried over magnesium sulfate. The solvents were distilled off and the resulting oil was subjected to silica gel chromatography using hexane/ethyl acetate (19/1, v/v) as developing solvent to obtain 7.71 g of 3-(2,2,3,3,3-pentafluoropropoxy)methyl-4-methyl-1-nitrobenzene having a melting point of 53.5°–54.5° C. in a 95.5% yield.

SYNTHESIS EXAMPLE 2

Synthesis of 3-(2,2,3,3,3-pentafluoropropoxy)methyl-4-methylaniline (the compound of formula (V) in which R is $CH_2CF_2CF_3$, $X^1$ is 4-$CH_3$ and $X^2$ is H)

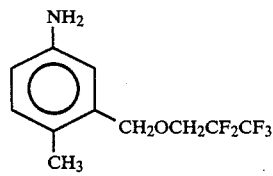

In 40 ml of ethanol, 7.30 g (0.0244 mol) of the nitro compound obtained in Synthesis Example 1 was dissolved. The solution was added with 0.1 g of 10% Pd-C and 3.66 g (0.073 mol) of hydrazine hydrate and refluxed on a hot water bath for one hour. After allowed to cool by itself, the solution was passed through a Celite layer to filter out the catalyst and then washed with ethanol. The filtrate was concentrated, dissolved in dichloromethane, washed with water, a saturated sodium bicarbonate aqueous solution and a saturated sodium chloride aqueous solution, and dried over anhydrous potassium carbonate. The solvents were distilled off and the residue was fractionally distilled, collecting the fraction having a boiling point of 82°–83° C. at 0.18 mmHg. There was obtained 6.09 g of 3-(2,2,3,3,3-pentafluoropropoxy)methyl-4-methylaniline in a 93% yield.

SYNTHESIS EXAMPLE 3

Synthesis of 4-[[3-(2,2,3,3,3-pentafluoropropoxy)methyl-4-methylphenyl]hydrazono]-2-phenyl-2-oxazolin-5-one (the compound of formula (II) in which R is $CH_2CF_2CF_3$, $X^1$ is 4-$CH_3$ and $X^2$, $Y^1$ and $Y^2$ are all H)

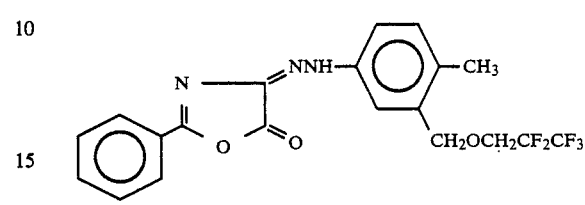

To a mixed solution of 6.9 ml of acetic acid and 1.8 ml of concentrated hydrochloric acid, was added 2.71 g (0.0101 mol) of the aniline derivative obtained in Synthesis Example 2, followed by dropwise addition of a solution of 0.729 g (0.0106 mol) of sodium nitrite in 2 ml of water at a temperature below 0° C. to prepare a diazonium salt solution.

Separately, 2.08 g (0.0116 mol) of hippuric acid was added to 5.7 ml (0.0604 mol) of acetic anhydride and stirred at 80° C. for 10 minutes to obtain a solution of 2-phenyl-2-oxazolin-5-one. This solution was cooled to −20° C. and added with 1.65 g of anhydrous sodium acetate.

To this solution was added the previously prepared diazonium salt solution under stirring, and the mixed solution was further stirred at −20° to −10° C. for 2 hours and then at room temperature for 5 hours. Thereafter, water was added to the solution and the precipitated crystals were filtered out, washed well with water and dried to obtain 3.65 g (82.2% yield) of 4-[[3-(2,2,3,3,3-pentafluoropropoxy)methyl-4-methylphenyl]hydrazono]-2-phenyl-2-oxazolin-5-one. Recrystallization thereof from methylenechloride-hexane gave the orange-colored needle crystals (m.p. 160°–161° C.).

EXAMPLE 1

Synthesis of 1-[3-(2,2,3,3,3-pentafluoropropoxy)methyl-4-methyl]phenyl-5-phenyl-1H-1,2,4-triazole-3-carboxamide (Compound No. 28)

In 46 ml of acetone, 3.30 g (7.5 mmol) of 4-[[3-(2,2,3,3,3-pentafluoropropoxy)methyl-4-methylphenyl]hydrazono]-2-phenyl-2-oxazolin-5-one obtained in Synthesis Example 3 was suspended. To this suspension was added 1.5 ml of concentrated ammonia water, followed by one-hour stirring. The resulting solution was made acid with 1.6 ml of concentrated hydrochloric acid and further stirred at 40° to 50° C. for 30 minutes. Acetone was distilled off and the residue was extracted with benzene. The organic layer was dried over anhydrous sodium sulfate and the solvents were distilled off to obtain a crude product. This crude product was purified by silica gel chromatography using $CH_2Cl_2$/MeOH (97/3, v/v) as developing solvent and further recrystallized to obtain 3.145 g (95.5% yield) of 1-[3-(2,2,3,3,3-pentafluoropropoxy)methyl-4-methyl]phenyl-5-phenyl-1H-1,2,4-triazole-3-carboxamide (m.p. 127°–129° C.).

EXAMPLE 2

Synthesis of 1-[4-methyl-3-[(3-methylbutoxy)methyl]phenyl]-5-phenyl-1H-1,2,4-triazole-3-carboxamide (Compound No. 27)

In 40 ml of acetone, 1.668 g (4.4 mmol) of 4-[[4-methyl-3-(3-methylbutoxy)methylphenyl]hydrazono]-2-phenyl-2-oxazolin-5-one synthesized in the similar way to Synthesis Examples 1-3 was suspended, followed by the addition of 1.3 ml of concentrated hydrochloric acid and one-hour stirring. The resulting solution was made acid by adding 1.5 ml of concentrated hydrochloric acid and further stirred at 40°-50° C. for 30 minutes. Acetone was distilled off and the residue was extracted with benzene. The organic layer was dried over anhydrous sodium sulfate and the solvents were distilled off to obtain a crude product. Purification of this crude product by silica gel chromatography using $CH_2Cl_2$/MeOH (97/3, v/v) as developing solvent and further recrystallization gave 1.498 g (90.0% yield) of 1-[4-methyl-3-[(3-methylbutoxy)methyl]phenyl]-5-phenyl-1H-1,2,4-triazole-3-carboxamide (m.p. 83°-85° C.).

EXAMPLE 3

Synthesis of 1-(3-butoxymethyl-4-chlorophenyl)-5-phenyl-1H-1,2,4-triazole-3-carboxamide (Compound No. 2)

In 10 ml of acetone, 1.157 g (3 mmol) of 4-[(3-butoxymethyl-4-chlorophenyl)hydrazono]-2-phenyl-2-oxazolin-5-one synthesized in the similar way to Synthesis Examples 1-3 was suspended, the suspension being then added with 0.6 ml of concentrated ammonia water and stirred at room temperature for 30 minutes. The resulting solution was made acid by adding 0.6 ml of concentrated hydrochloric acid and further stirred at 50° C. for 30 minutes. Acetone was distilled off and the residue was extracted by adding benzene and water. The organic layer was washed with a saturated sodium chloride aqueous solution and dried over anhydrous sodium sulfate. The solvents were distilled off to obtain a crude product. This crude product was purified by silica gel chromatography using hexane/ethyl acetate (½, v/v) as developing solvent and further recrystallized to obtain 1.087 g (94.2% yield) of 1-(3-butoxymethyl-4-chlorophenyl)-5-phenyl-1H-1,2,4-triazole-3-carboxamide (m.p. 96°-98° C.).

EXAMPLE 4

Synthesis of 1-[4-chloro-3-[(3-methylbutoxy)methyl]phenyl]-5-(2-fluorophenyl)-1H-1,2,4-triazole-3-carboxamide (Compound No. 23)

In 10 ml of acetone, 1.294 g (3 mmol) of 4-[4-chloro-3-[(3-methylbutoxy)methyl]phenyl hydrazono]-2-(2-fluorophenyl)-2-oxazolin-5-one synthesized in the similar way to Synthesis Examples 1-3 was suspended, followed by the addition of 0.6 ml of concentrated ammonia water and 30-minute stirring at room temperature. The resulting solution was made acid by adding 0.6 ml of concentrated hydrochloric acid and further stirred at 50° C. for 30 minutes. Acetone was distilled off and the residue was extracted by adding benzene and water. The organic layer was washed with a saturated sodium chloride aqueous solution and dried over anhydrous sodium sulfate. The solvents were distilled off to obtain a crude product, and this crude product was purified by subjecting it to silica gel chromatography using hexane/ethyl acetate (½, v/v) as developing solvent and recrystallized from ethyl acetate-hexane to obtain 1.062 g (82.3% yield) of 1-[4-chloro-3-[(3-methylbutoxy)methyl]phenyl]-5-(2-flurophenyl)-1H-1,2,4-triazole-3-carboxamide (m.p. 113°-115° C.).

EXAMPLE 5

Preparation of Wettable Powder

Compound No. 4 (50 parts), a salt of lignin sulfonic acid (5 parts), a salt of alkylsulfonic acid (3 parts) and diatomaceous earth (42 parts) are mixed and pulverized to form a wettable powder. The wettable powder is diluted with water when used.

EXAMPLE 6

Preparation of Emulsion

Compound No. 27 (25 parts), xylene (65 parts) and polyoxyethylene alkylaryl ether (10 parts) are uniformly mixed to form an emulsion. The emulsion is diluted with water when used.

EXAMPLE 7

Preparation of Granules

Compound No. 13 (8 parts), bentonite (40 parts), clay (45 parts) and a salt of lignin sulfonic acid (7 parts) are uniformly mixed, further kneaded by adding water, worked into granules by an extrusion granulator and dried.

In the following, the test examples on the compounds of the present invention will be given to show their selective herbicidal activities.

For the sake of comparison, a herbicidal composition having as its active ingredient a compound having the following formula disclosed in Japanese Patent Application Kokai (Laid-Open) No. 98004/84 was also tested as comparative example.

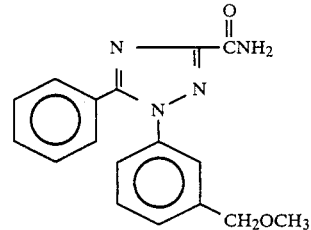

TEST EXAMPLE 1

Effect on Crop Field Weeds (Pre-emergence Treatment)

In a planters (650×210×220 mm) having soil placed therein simulating a field, a predetermined amount of the seeds of *Amaranthus retroflexus, Bidens pilosa* var. *pilosa, Brassica arvensis, Stellaria media, Solanum nigrum, Abutilon theophrasti, Echinochloa Crus-galli* var. *frumentacea, Digitaria sanguinalis,* wheat and corn were sown and covered up with soil. Then the wettable powder prepared in the same manner as Example 5 described above was diluted with water to a prescribed concentration and was sprayed uniformly over the soil surface by a spray gun in such an amount that the active ingredient would be applied to the soil at a rate of 200 g/10 a. Thereafter, the planters were placed and kept in a glasshouse for giving the best atmosphere for the growth of said plants.

Twenty-one days after said treatment, the herbicidal effect of each compounds on the respective weeds and the phytotoxicity to the crops by the compounds were observed and evaluated according to the following ratings. The results are shown in Table 3.

Ratings for Evaluation

0 ... no herbicidal effect
1 ... not more than 30% herbicidal effect
2 ... 31-50% herbicidal effect
3 ... 51-70% herbicidal effect
4 ... 71-90% herbicidal effect
5 ... 91-100% herbicidal effect Degree of Phytotoxicity

| — ... none | ± ... slight |
| --- | --- |
| + ... medium | ++ ... great |
| +++ ... serious | |

TABLE 3

| Compound No. | Amaranthus retroflexus | Bidens pilosa var. pilosa | Brassica arvensis | Stellaria media | Solanum nigrum | Abutilon theophrasti | Echinochloa Crusgalli var. frumentacea | Digitaria sanguinalis | Wheat | Corn |
| --- | --- | --- | --- | --- | --- | --- | --- | --- | --- | --- |
| 1 | 5 | 5 | 5 | 5 | 5 | 5 | 5 | 5 | — | ± |
| 2 | 5 | 5 | 5 | 5 | 5 | 5 | 5 | 5 | — | ± |
| 3 | 5 | 5 | 5 | 5 | 5 | 5 | 5 | 5 | — | ± |
| 4 | 5 | 5 | 5 | 5 | 5 | 5 | 5 | 5 | — | ± |
| 5 | 5 | 5 | 5 | 5 | 5 | 5 | 5 | 5 | — | ± |
| 6 | 5 | 5 | 5 | 5 | 5 | 5 | 5 | 5 | — | ± |
| 7 | 5 | 5 | 5 | 5 | 5 | 5 | 5 | 5 | — | ± |
| 8 | 4 | 5 | 5 | 5 | 4 | 4 | 5 | 5 | — | — |
| 9 | 4 | 5 | 5 | 5 | 4 | 3 | 5 | 5 | — | — |
| 10 | 5 | 5 | 5 | 5 | 5 | 4 | 5 | 5 | — | — |
| 11 | 5 | 5 | 5 | 5 | 5 | 5 | 5 | 5 | — | ± |
| 12 | 5 | 5 | 5 | 5 | 5 | 5 | 5 | 5 | — | ± |
| 13 | 5 | 5 | 5 | 5 | 5 | 5 | 5 | 5 | — | ± |
| 14 | 5 | 5 | 5 | 5 | 5 | 5 | 5 | 5 | — | ± |
| 15 | 5 | 5 | 5 | 5 | 5 | 5 | 5 | 5 | ± | ± |
| 16 | 5 | 5 | 5 | 5 | 5 | 5 | 5 | 5 | — | ± |
| 17 | 5 | 5 | 5 | 5 | 5 | 5 | 5 | 5 | — | ± |
| 18 | 5 | 5 | 5 | 5 | 5 | 5 | 5 | 5 | — | ± |
| 19 | 5 | 5 | 5 | 5 | 5 | 5 | 5 | 5 | — | ± |
| 20 | 5 | 5 | 5 | 5 | 5 | 5 | 5 | 5 | — | — |
| 21 | 5 | 5 | 5 | 5 | 5 | 4 | 4 | 4 | — | — |
| 22 | 5 | 5 | 5 | 5 | 5 | 5 | 4 | 3 | — | — |
| 23 | 5 | 5 | 5 | 5 | 5 | 5 | 5 | 5 | — | ± |
| 24 | 5 | 5 | 5 | 5 | 5 | 5 | 5 | 5 | — | ± |
| 25 | 5 | 5 | 5 | 5 | 5 | 5 | 5 | 5 | — | ± |
| 26 | 5 | 5 | 5 | 5 | 5 | 5 | 5 | 5 | — | ± |
| 27 | 5 | 5 | 5 | 5 | 5 | 5 | 5 | 5 | — | ± |
| 28 | 5 | 5 | 5 | 5 | 5 | 5 | 5 | 5 | — | ± |
| 29 | 5 | 5 | 5 | 5 | 5 | 5 | 5 | 5 | — | ± |
| 30 | 5 | 5 | 5 | 5 | 5 | 5 | 4 | 4 | — | — |
| 31 | 5 | 4 | 5 | 5 | 5 | 4 | 4 | 4 | — | ± |
| 32 | 5 | 5 | 5 | 5 | 5 | 5 | 5 | 5 | — | ± |
| 33 | 5 | 5 | 5 | 5 | 5 | 5 | 5 | 5 | — | ± |
| 34 | 5 | 5 | 5 | 5 | 5 | 5 | 5 | 5 | — | ± |
| 35 | 5 | 5 | 5 | 5 | 5 | 5 | 5 | 5 | — | ± |
| 36 | 5 | 5 | 5 | 5 | 5 | 4 | 4 | 5 | — | — |
| 37 | 5 | 5 | 5 | 5 | 5 | 4 | 4 | 4 | — | — |
| 38 | 5 | 5 | 5 | 5 | 5 | 5 | 4 | 5 | — | — |
| 39 | 5 | 5 | 5 | 5 | 5 | 5 | 5 | 5 | — | ± |
| 40 | 5 | 5 | 5 | 5 | 5 | 5 | 5 | 5 | — | ± |
| 41 | 5 | 5 | 5 | 5 | 5 | 5 | 5 | 5 | — | ± |
| 42 | 5 | 5 | 5 | 5 | 5 | 5 | 5 | 5 | — | ± |
| 43 | 5 | 5 | 5 | 5 | 5 | 5 | 5 | 5 | — | ± |
| 44 | 5 | 5 | 5 | 5 | 5 | 5 | 4 | 5 | — | — |
| 45 | 5 | 5 | 5 | 5 | 5 | 5 | 5 | 5 | — | — |
| 46 | 5 | 5 | 5 | 5 | 5 | 5 | 5 | 5 | — | — |
| 47 | 5 | 5 | 5 | 5 | 5 | 5 | 5 | 5 | — | ± |
| 48 | 5 | 5 | 5 | 5 | 5 | 5 | 5 | 5 | — | — |
| Comp. Example | 1 | 1 | 2 | 2 | 1 | 1 | 0 | 0 | — | — |

TEST EXAMPLE 2

Effect on Crop Field Weeds (Post-Emergence Treatment)

By following the procedures in Test Example 1, the seeds of the specified plants were sown in the planters. When the plants grew to the one- to two-foliage stage, the same wettable powders as used in Test Example 1 and likewise diluted with water were uniformly sprayed to the stalks and leaves of the plants and on the soil surface in the planters by a spray gun so that the active ingredient would be applied at a rate of 200 g/10 a. Then the planters were kept in the glasshouse.

Twenty-one days after said treatment, the herbicidal effect of the compositions on the weeds and phytotoxicity of the crops were observed and evaluated in the same way as in Test Example 1. The results are shown in Table 4.

*gittaria pygmaea* and *Cyperus serotinus* were planted. Further, the two bifoliage seedlings of rice plant (variety: Sasanishiki) were transplanted in a pot. After keeping the pots in a hothouse for three days, the emulsions prepared in the similar way to Example 6 and diluted

TABLE 4

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 1  | 5 | 5 | 5 | 5 | 5 | 4 | 2 | 3 | — | ± |
| 2  | 5 | 5 | 5 | 5 | 5 | 5 | 2 | 4 | — | ± |
| 3  | 5 | 5 | 5 | 5 | 5 | 4 | 2 | 3 | — | ± |
| 4  | 5 | 5 | 5 | 5 | 5 | 4 | 2 | 2 | — | ± |
| 5  | 4 | 5 | 5 | 5 | 4 | 3 | 2 | 2 | — | ± |
| 6  | 5 | 5 | 5 | 5 | 5 | 5 | 2 | 5 | — | ± |
| 7  | 5 | 5 | 5 | 5 | 5 | 5 | 3 | 3 | — | ± |
| 8  | 4 | 5 | 5 | 5 | 3 | 3 | 2 | 2 | — | — |
| 9  | 4 | 5 | 5 | 5 | 4 | 3 | 2 | 2 | — | — |
| 10 | 4 | 5 | 5 | 5 | 4 | 4 | 3 | 2 | — | — |
| 11 | 5 | 5 | 5 | 5 | 5 | 5 | 2 | 2 | — | ± |
| 12 | 5 | 5 | 5 | 5 | 5 | 5 | 2 | 5 | — | ± |
| 13 | 5 | 5 | 5 | 5 | 5 | 5 | 4 | 5 | — | ± |
| 14 | 5 | 5 | 5 | 5 | 5 | 5 | 5 | 5 | ± | ± |
| 15 | 5 | 5 | 5 | 5 | 5 | 5 | 5 | 5 | + | ++ |
| 16 | 5 | 5 | 5 | 5 | 5 | 5 | 5 | 5 | ± | + |
| 17 | 5 | 5 | 5 | 5 | 5 | 4 | 2 | 2 | — | ± |
| 18 | 5 | 5 | 5 | 5 | 5 | 5 | 2 | 3 | — | ± |
| 19 | 5 | 5 | 5 | 5 | 5 | 3 | 2 | 3 | — | ± |
| 20 | 5 | 5 | 5 | 5 | 4 | 3 | 2 | 2 | — | — |
| 21 | 4 | 4 | 5 | 5 | 4 | 2 | 3 | 2 | — | — |
| 22 | 4 | 5 | 5 | 4 | 5 | 2 | 2 | 2 | — | — |
| 23 | 5 | 5 | 5 | 5 | 5 | 5 | 2 | 2 | — | ± |
| 24 | 5 | 5 | 5 | 5 | 5 | 5 | 5 | 5 | + | + |
| 25 | 5 | 5 | 5 | 5 | 4 | 3 | 2 | 2 | — | ± |
| 26 | 5 | 5 | 5 | 5 | 4 | 4 | 2 | 3 | — | ± |
| 27 | 5 | 5 | 5 | 5 | 5 | 4 | 4 | 3 | — | ± |
| 28 | 5 | 5 | 5 | 5 | 5 | 5 | 2 | 5 | — | ± |
| 29 | 5 | 5 | 5 | 5 | 5 | 3 | 2 | 5 | — | ± |
| 30 | 5 | 5 | 5 | 5 | 5 | 4 | 2 | 4 | — | — |
| 31 | 5 | 5 | 5 | 5 | 5 | 4 | 3 | 4 | — | ± |
| 32 | 5 | 5 | 5 | 5 | 5 | 5 | 4 | 5 | — | ± |
| 33 | 5 | 5 | 5 | 5 | 5 | 5 | 4 | 5 | — | ± |
| 34 | 5 | 5 | 5 | 5 | 5 | 4 | 2 | 4 | — | — |
| 35 | 5 | 5 | 5 | 5 | 5 | 5 | 4 | 5 | — | ± |
| 36 | 5 | 5 | 5 | 5 | 5 | 4 | 4 | 4 | — | ± |
| 37 | 4 | 5 | 5 | 3 | 4 | 4 | 2 | 2 | — | — |
| 38 | 4 | 5 | 5 | 5 | 5 | 4 | 2 | 2 | — | — |
| 39 | 5 | 5 | 5 | 5 | 5 | 5 | 3 | 3 | — | — |
| 40 | 5 | 5 | 5 | 5 | 5 | 5 | 3 | 4 | — | ± |
| 41 | 5 | 5 | 5 | 5 | 5 | 4 | 3 | 3 | — | — |
| 42 | 5 | 5 | 5 | 5 | 5 | 5 | 3 | 3 | — | — |
| 43 | 5 | 5 | 5 | 5 | 5 | 5 | 4 | 4 | — | ± |
| 44 | 5 | 5 | 5 | 5 | 5 | 4 | 2 | 3 | — | — |
| 45 | 5 | 5 | 5 | 5 | 5 | 5 | 2 | 4 | — | — |
| 46 | 5 | 5 | 5 | 5 | 5 | 5 | 4 | 5 | — | ± |
| 47 | 5 | 5 | 5 | 5 | 5 | 5 | 4 | 5 | ± | ± |
| 48 | 5 | 5 | 5 | 5 | 5 | 5 | 4 | 5 | — | ± |
| Comp. Example | 2 | 1 | 1 | 1 | 0 | 0 | 0 | 0 | — | — |

TEST EXAMPLE 3

Effect on Paddy Field Weeds and Phytotoxicity to Rice Plant

In the 1/2000-are Wagner pots packed with paddy soil and further filled with water, the seeds of *Echinochloa Crus-galli* var. hispidula, *Scirpus juncoides* subsp. Hotarui, *Alisma canaliculatum*, *Monochoria vaginalis* and *Cyperus difformis* were sown and the tubers of *Sa-* with water to a predetermined concentration were trickled down uniformly onto the water surface so that the active ingredient would be applied at a rate of 200 g/10 a.

Twenty-one days after said treatment, the herbicidal effect and the degree of phytotoxicity to the rice plants by the compounds were examined in the same way as in Test Example 1. The results are shown in Table 5.

TABLE 5

| Compound No. | Echinochloa Crus-galli var. hispidula | Scirpus juncoides subsp. Hotarui | Alisma canaliculatum | Manochloria vaginalis | Cyperus difformis | Sagittaria pygmaea | Cyperus serotinus | rice plant |
|---|---|---|---|---|---|---|---|---|
| 1 | 5 | 4 | 5 | 5 | 5 | 5 | 5 | — |
| 2 | 5 | 5 | 5 | 5 | 5 | 5 | 5 | — |
| 3 | 5 | 5 | 5 | 5 | 5 | 5 | 5 | — |
| 4 | 5 | 5 | 5 | 5 | 5 | 5 | 5 | — |
| 5 | 5 | 5 | 5 | 5 | 5 | 5 | 5 | — |
| 6 | 5 | 5 | 5 | 5 | 5 | 5 | 5 | — |
| 7 | 5 | 4 | 5 | 5 | 5 | 5 | 5 | — |
| 8 | 5 | 5 | 5 | 5 | 5 | 5 | 5 | — |
| 9 | 5 | 4 | 5 | 5 | 5 | 5 | 5 | — |
| 10 | 5 | 5 | 5 | 5 | 5 | 5 | 5 | — |
| 11 | 5 | 5 | 5 | 5 | 5 | 5 | 5 | — |
| 12 | 5 | 5 | 5 | 5 | 5 | 5 | 5 | — |
| 13 | 5 | 5 | 5 | 5 | 5 | 5 | 5 | — |
| 14 | 5 | 5 | 5 | 5 | 5 | 5 | 5 | — |
| 15 | 5 | 5 | 5 | 5 | 5 | 5 | 5 | — |
| 16 | 5 | 5 | 5 | 5 | 5 | 5 | 5 | — |
| 17 | 5 | 5 | 5 | 5 | 5 | 5 | 5 | — |
| 18 | 5 | 5 | 5 | 5 | 5 | 5 | 5 | — |
| 19 | 5 | 5 | 5 | 5 | 5 | 5 | 5 | — |
| 20 | 5 | 4 | 5 | 5 | 5 | 5 | 5 | — |
| 21 | 5 | 4 | 4 | 4 | 5 | 4 | 5 | — |
| 22 | 5 | 4 | 5 | 5 | 5 | 5 | 5 | — |
| 23 | 5 | 5 | 5 | 5 | 5 | 5 | 5 | — |
| 24 | 5 | 5 | 5 | 5 | 5 | 5 | 5 | — |
| 25 | 5 | 5 | 5 | 5 | 5 | 5 | 5 | — |
| 26 | 5 | 5 | 5 | 5 | 5 | 5 | 5 | — |
| 27 | 5 | 5 | 5 | 5 | 5 | 5 | 5 | — |
| 28 | 5 | 5 | 5 | 5 | 5 | 5 | 5 | — |
| 29 | 5 | 5 | 5 | 5 | 5 | 5 | 5 | — |
| 30 | 5 | 3 | 4 | 5 | 5 | 5 | 4 | — |
| 31 | 5 | 4 | 5 | 5 | 5 | 5 | 4 | — |
| 32 | 5 | 5 | 5 | 5 | 5 | 5 | 5 | — |
| 33 | 5 | 5 | 5 | 5 | 5 | 5 | 5 | — |
| 34 | 5 | 5 | 5 | 5 | 5 | 5 | 5 | — |
| 35 | 5 | 5 | 5 | 5 | 5 | 5 | 5 | — |
| 36 | 5 | 5 | 5 | 5 | 5 | 5 | 5 | — |
| 37 | 5 | 5 | 5 | 5 | 5 | 5 | 4 | — |
| 38 | 5 | 5 | 5 | 5 | 5 | 4 | 4 | — |
| 39 | 5 | 5 | 5 | 5 | 5 | 5 | 5 | — |
| 40 | 5 | 5 | 5 | 5 | 5 | 5 | 5 | — |
| 41 | 5 | 5 | 5 | 5 | 5 | 5 | 5 | — |
| 42 | 5 | 5 | 5 | 5 | 5 | 5 | 5 | — |
| 43 | 5 | 5 | 5 | 5 | 5 | 5 | 5 | — |
| 44 | 5 | 3 | 5 | 5 | 5 | 5 | 5 | — |
| 45 | 5 | 4 | 5 | 5 | 5 | 5 | 5 | — |
| 46 | 5 | 5 | 5 | 5 | 5 | 5 | 5 | — |
| 47 | 5 | 5 | 5 | 5 | 5 | 5 | 5 | — |
| 48 | 5 | 5 | 5 | 5 | 5 | 5 | 5 | — |
| Comp. Example | 0 | 0 | 1 | 0 | 0 | 1 | 0 | — |

What is claimed is:

1. A derivative of 1,5-diphenyl-1H-1,2,4-triazole-3-carboxamide represented by the formula (I):

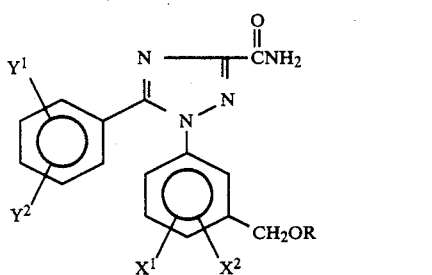

wherein R is a straight-chain alkyl group having 2 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; and $Y^2$ is a hydrogen or a fluorine.

2. The derivative according to claim 1, wherein R is a straight-chain alkyl group having 3 to 6 carbon atoms which is non-substituted or substituted with 3 to 12 fluorine atoms, a branched alkyl group having 4 to 7 carbon atoms which is non-substituted or substituted with 3 to 12 fluorine atoms, a cyclic alkyl group having 4 to 7 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; and $Y^2$ is a hydrogen or a fluorine.

3. The derivative according to claim 2, wherein R is a straight-chain alkyl group having 2 to 4 carbon atoms which is substituted with 3 to 7 fluorine atoms, $X^1$ is a chlorine or a methyl group, and $X^2$, $Y^1$ and $Y^2$ are hydrogens.

4. The derivative according to claim 3, wherein said derivative is 1-[3-(2,2,2-trifluoroethoxy)methyl4-chloro]phenyl-5-phenyl-1H-1,2,4-triazole-3-carboxamide.

5. The derivative according to claim 3, wherein said derivative is 1-[3-(2,2,4,4-tetrafluoropropoxy)methyl-4-chloro]-phenyl-5-phenyl-1H-1,2,4-triazole-3-carboxamide.

6. The derivative according to claim 3, wherein said derivative is 1-[3-(2,2,3,3,3-pentafluoropropoxy)-methyl-4-chloro]-phenyl-5-phenyl-1H-1,2,4-triazole-3-carboxamide.

7. The derivative according to claim 3, wherein said derivative is 1-[3-(2,2,3,4,4,4-hexafluorobutoxy)-methyl-4-chloro]-phenyl-5-phenyl-1H-1,2,4-triazole-3-carboxamide.

8. The derivative according to claim 3, wherein said derivative is 1-[3-(2,2,3,3,4,4,4-heptafluorobutoxy)-methyl-4-chloro]phenyl-5-phenyl-1H-1,2,4-triazole-3-carboxamide.

9. The derivative according to claim 3, wherein said derivative is 1-[3-(2,2,3,3,3-pentafluoropropoxy)-methyl-4-methyl]phenyl-5-phenyl-1H-1,2,4-triazole-3-carboxamide.

10. A herbicidal composition comprising as active ingredient a herbicidally effective amount of a derivative of 1,5-diphenyl-1H-1,2,4-triazole-3-carboxamide represented by the formula (I):

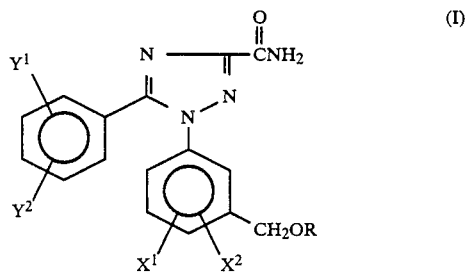

wherein R is a straight-chain alkyl group having 2 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluroine; and $Y^2$ is a hydrogen or a fluorine, and herbicidally acceptable carrier or adjuvant.

* * * * *